United States Patent [19]

Tsuda

[11] Patent Number: 4,938,055
[45] Date of Patent: Jul. 3, 1990

[54] APPARATUS FOR TESTING ABRASION

[75] Inventor: Isami Tsuda, Kobe, Japan

[73] Assignee: Ozeki Chemical Industry Co., Ltd., Kobe, Japan

[21] Appl. No.: 301,943

[22] Filed: Jan. 26, 1989

[51] Int. Cl.$^5$ ............................................. G01N 19/00
[52] U.S. Cl. ............................................ 73/8; 73/146
[58] Field of Search ...................................... 73/8, 146

[56] References Cited

U.S. PATENT DOCUMENTS

| 1,638,111 | 8/1937 | Coffin | 73/8 |
| 3,119,257 | 1/1964 | Speer | 73/146 |
| 3,316,758 | 5/1967 | Wild | 73/146 |

FOREIGN PATENT DOCUMENTS

| 2611123 | 9/1977 | Fed. Rep. of Germany | 73/146 |
| 479978 | 12/1975 | U.S.S.R. | 73/146 |
| 1151640 | 4/1985 | U.S.S.R. | 73/146 |

Primary Examiner—Hezron E. Williams
Assistant Examiner—Joseph W. Roskos
Attorney, Agent, or Firm—Wenderoth, Lind & Ponack

[57] ABSTRACT

The present invention relates to an abrasion tester, and in particular to an abrasion tester capable of testing abrasion or breakage of a road generated by the travel of cars in the winter or summer under actual road conditions. The tester includes a turntable rotatably supported in the apparatus for receiving test pieces, a cooling or high temperature chamber confronting the turntable so as to subject the test pieces to high or low temperatures, and a rotatable grinding member movable into and out of contact with the test pieces. Thus, when the grinding member is brought into contact with a test piece and is rotated, the turntable rotates to simulate travel of the grinding member on the test piece. Further, rotation of the turntable moves the test pieces through the chamber where they are subjected to appointed temperature conditions.

7 Claims, 3 Drawing Sheets

APPARATUS FOR TESTING ABRASION

BACKGROUND OF THE INVENTION

The present invention relates to an apparatus for testing abrasion, and in particular to an apparatus for testing abrasion capable of simulating real road conditions to test abrasion or breakage of a road generated by the travel of cars in the winter or summer.

In particular, in a cold area dust pollution has resulted from the use of studded tires or the cracking of a road due to a difference in temperature during the winter season and the summer season. Thus, not only has such brought about the improvement of studded tires and the like but also the research of road materials giving rise to no such deleterious effects even under such conditions.

However, even though road materials exhibiting satisfactory characteristics have been developed, an apparatus capable of carrying out a test simulative of an actual road surface has hardly been found, so that in general, a method of testing an actual road to observe results has been used in many cases.

In addition, the road materials include those for use in a cold area and high temperature-resisting ones aimed at preventing a road surface from flowing, so that it has been required in the testing of these road materials to set a tester at lower or higher temperatures, whereby problems have occurred in that much time was required and costs associated therewith were high.

SUMMARY OF THE INVENTION

In view of the above-described problems, the present inventors have developed the present invention from results of their investigations aimed at providing an apparatus for testing abrasion capable of being simply set to carry out the testing at low or high temperatures of road materials for use in a cold area and for use in higher temperatures.

That is to say, the present invention is drawn to an apparatus for testing abrasion in which a main body of a turntable is provided thereon with a work table having a diameter smaller than that of said main body of said turntable, a test piece-inserting portion is formed above the main body of the turntable outside of said work table, a cooling or high-temperature chamber is disposed over a semicircular portion of said main body of the turntable, the main body of the turntable is provided with a grinding member capable of moving up and down on a side of the turntable opposite said cooling or high-temperature chamber, and the grinding member driven at an appointed speed and under an appointed load is brought into contact with the test pieces on the turntable under the lower- or higher-temperature condition to test the degree to which the test pieces are ground.

With the tester according to the present invention, the lower temperatures and the higher temperatures can be easily changed over. And the grinding member is not limited to a studded tire, that is, other grinding members adapted to test actual conditions may be employed.

Generally then, the apparatus according to the present invention comprises the main body of the turntable provided with the chamber capable of receiving the test pieces of road material therein and cooling or heating the test pieces, and the grinding member capable of moving up and down and being set to a rotational speed and load.

DETAILED DESCRIPTION OF THE PREFERRED EMBODIMENT

Figure 1:
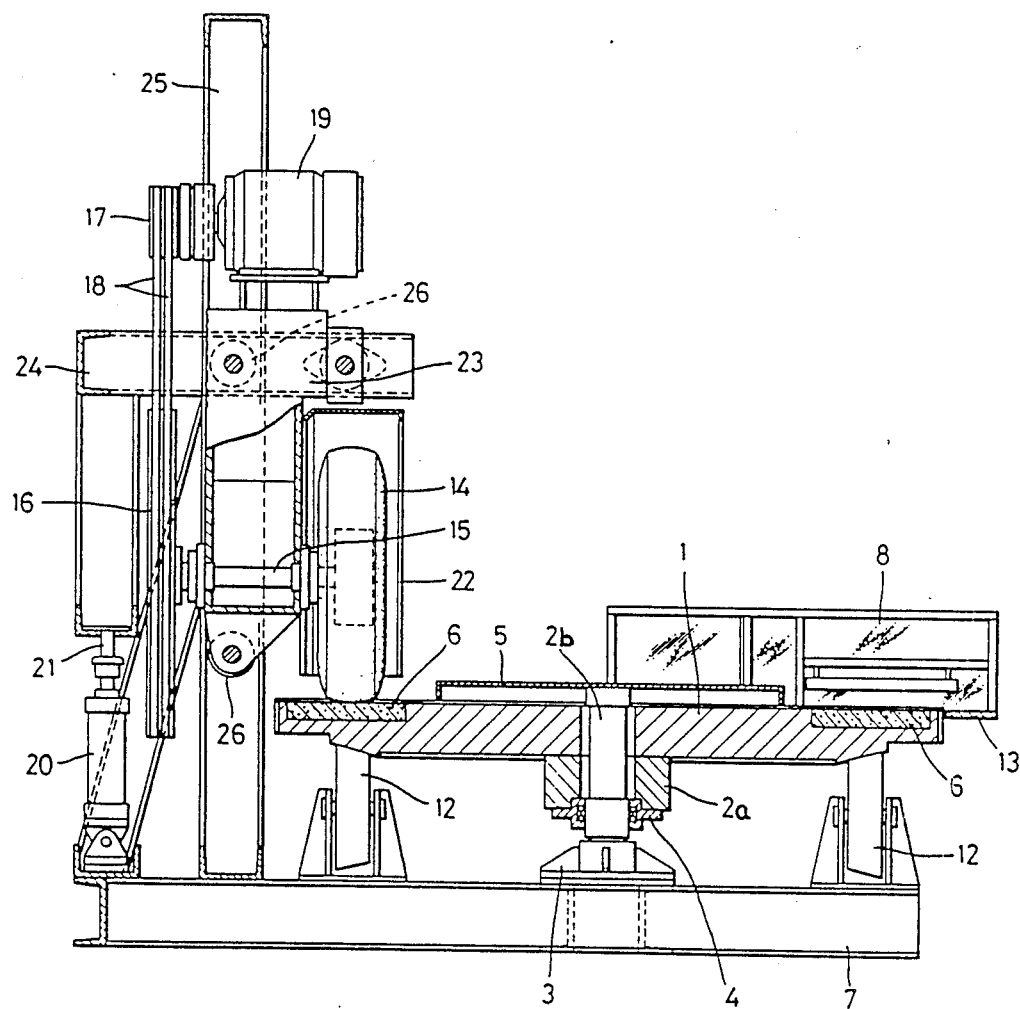
FIG. 1 is a side view of an abrasion tester according to the present invention.

Referring now to FIG. 1, reference numeral 1 designates a main body of a turntable fixedly mounted to a shaft stand 2a supported on a base frame 7 by means of a turntable shaft 2b through a flange unit 4. And, a work table 5 having a diameter smaller than that of said main body 1 is disposed over the main body 1 of the turntable. A plurality of road material test pieces 6 (hereinafter called test pieces 6 for short) are inserted in a recess formed around said work table 5, the test pieces 6 having an arcuate shape.

In addition, reference numeral 8 designates a semicircular chamber provided at an upper surface of the main body 1 of the turntable and fixedly mounted on the work table 5 and an outer frame 13 of the main body 1 of the turntable. And, this chamber 8 is provided with a nozzle 9 for releasing liquefied nitrogen and a heater 10 in a ceiling portion thereof so that said chamber 8 may be used as a cooling or high-temperature chamber. A temperature at which the chamber 8 serves as the cooling chamber or the high-temperature chamber is selected on an automatic control panel (not shown) and a thermocouple (not shown) disposed on a side surface of the chamber 8 senses when the chamber 8 arrives at the temperature to operate a switch.

In addition, reference numeral 11 designates a geared motor for rotating the turntable to turn the main body 1 of the turntable into the cooling chamber or the high-temperature chamber having an appointed temperature by means of liquified nitrogen or the heater, whereby the selected temperature is imparted to all test pieces 6 disposed in an outer peripheral portion of the main body 1 of the turntable. At this time, a rubber-lined wheel 12, which is disposed on the base frame 7 in contact with a lower surface of the main body 1 of the turntable, assists the rotation of the turntable.

Next, reference number 14 designates a grinding member for directly imparting pressure to and abrading the test piece (a studded tire in this drawing), said grinding member 14 being connected with a V-pulley 16 by means of a shaft 15 so as to be rotated by means of a V-belt 18 reeved around another V-pulley 17 directly connected to a driving motor 19.

And, in FIG. 1 the grinding member 14 is shown in contact with a test piece 6. But the grinding member 14 is rotatably supported by a support arm 23 which is directly connected to a sample cover 22. An L-shaped support arm 24 is connected to a floating joint 21 so as to move up and down together with the grinding member 14, the V-pulleys 16, 17, the driving motor 19 and the V-belt 18 rotating said grinding member 14, by means of guide rollers 26 respectively guided at both sides of a support bracket 25 and slid therealong via the floating joint 21 by means of a pressure air cylinder 20.

Thus, an appointed rotational speed and load are applied to the grinding member 14 to rotate the grinding member 14 and bring the same into contact with the test pieces 6 on the main body 1 of the turntable set at a selected temperature. Thereupon, the main body 1 of the turntable is rotated at a speed corresponding to the rotation speed of the grinding member 14. Here, a frictional rotation is carried out between the test pieces 6 and the grinding member 14 for an appointed time so as to be able to determine the degree to which the test pieces 6 abrade.

Although the means for setting the various conditions in the apparatus according to the present invention is not shown, such comprises the automatic control panel described above.

The apparatus according to the present invention has the above-described structure and is characterized in that abrasion tests at both lower temperatures and higher temperatures for the test pieces 6 can be easily changed over.

That is to say, a pipe from a liquefied nitrogen cylinder (not shown) is connected with the nozzle 9 for use with liquefied nitrogen, an appointed temperature being selected by means of the automatic control panel, and liquefied nitrogen gas is injected into the chamber 8 to easily cool the interior of the chamber 8 until the interior reaches the appointed temperature. In this cooling process the test piece 6 on the main body 1 of the turntable can be cooled as a whole to a uniform temperature in a short time if the main body 1 of the turntable in which the test piece 6 is disposed is rotated by means of the geared motor 11.

And then, the main body 1 of the turntable is stopped and simultaneously the grinding member 14, which is rotating at the appointed speed, is lowered into contact with the test piece 6 at the appointed load, whereby the test piece 6 is rotated to observe the degree to which the test piece 6 abrades after an appointed time.

In addition, in the case where the test piece 6 is tested at higher temperatures, the temperature of the inside of the chamber 8 is raised by means of the heater 10 disposed in the chamber 8. And, the main body 1 of the turntable, in which the test piece 6 is disposed, is subjected to a levelling operation so that the test piece 6 may reach the appointed temperature as a whole. Then, the abrasion test by means of the grinding member 14 is carried out in the same manner as in said case at lower temperatures.

Thus, in the apparatus according to the present invention both the nozzle for use with liquefied nitrogen and the heater are disposed within the chamber 8 on the main body 1 of the turntable so that the testing at lower temperatures can be changed over to that at higher temperatures by merely regulating only the inside of the chamber 8, and vice versa. Accordingly, an improvement in test efficiency, reliability and a reduction in size of the tester as compared with the conventional test methods and equipment can be achieved.

In addition, in the conventional testers, the test piece stands still while only the abrasion member, such as a tire, is rotated and two or more tires have been used, whereby a considerable pressure and a cylinder have been required. On the contrary, with the apparatus according to the present invention, the turntable in which the test piece is disposed is rotated in a horizontal plane with the test piece in contact with the grinding member. Thus, an advantage occurs in that the load applied to the grinding member can be reduced.

A long wave-infrared heater is most preferably used as the heater 10 disposed within the chamber 8 in the apparatus according to the present invention in view of the influence of sunlight upon the road surface but other heaters that discharge hot air, such as fuel jet heater and electric drier, and a conventional electric heater can also be used.

Figure 2:
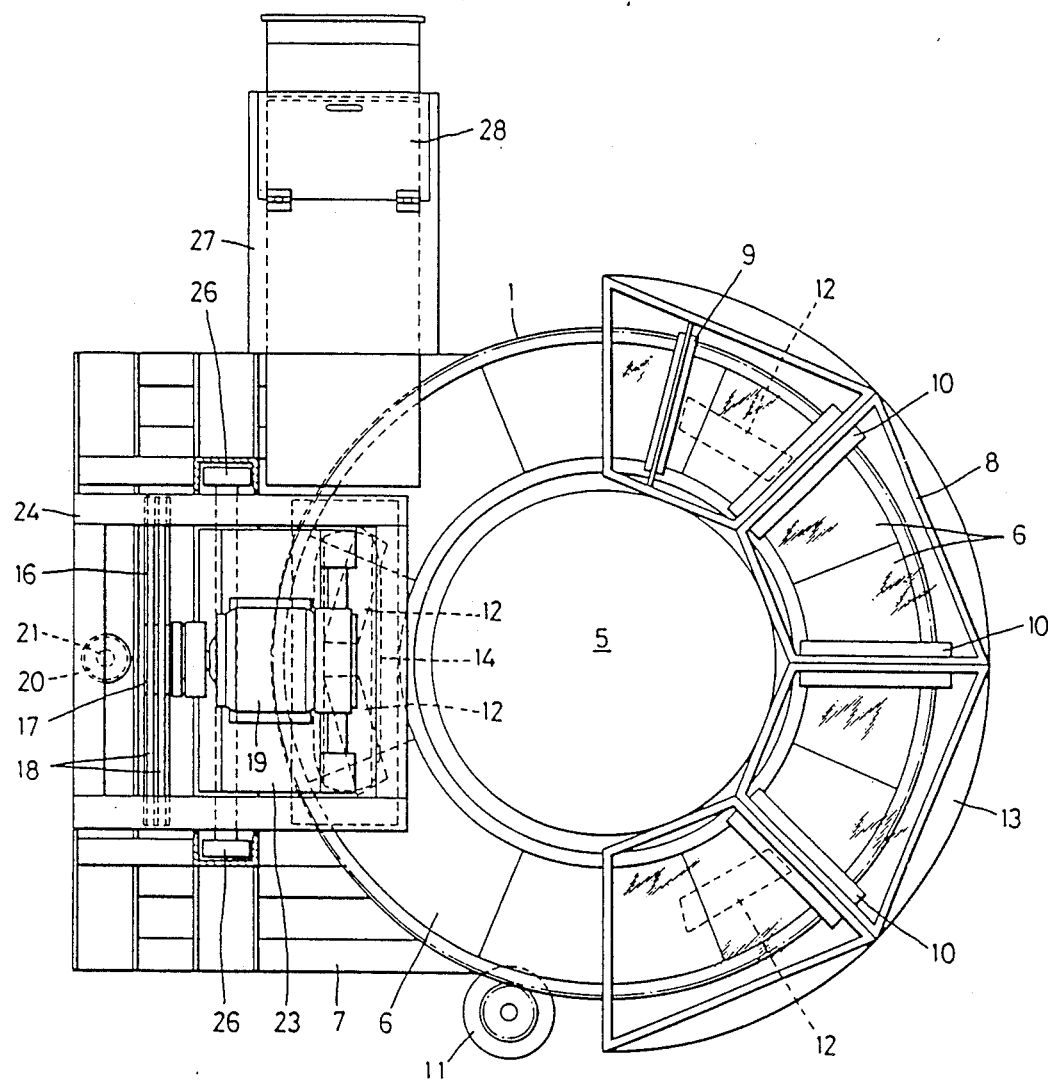
FIG. 2 is a plan view thereof.
Figure 3:
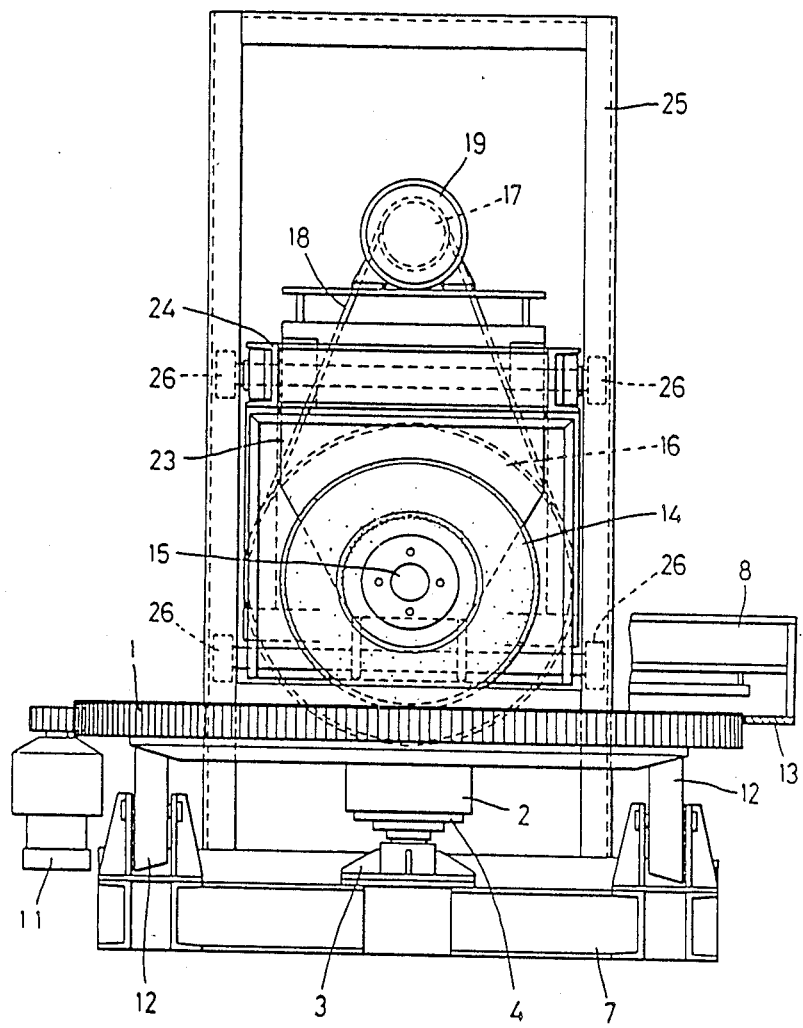
FIG. 3 is a front view thereof.

According to the present invention, dust generated during the abrasion test are sucked by means of a dust collector 27 disposed at the lower reaches of the grinding member 14, as shown in FIG. 2, to remove pulverized powders by means of a filter 28 and sucked air is discharged by means of a duct mounted on said dust collector.

In addition, according to the present invention, the grinding member 14 is not limited by the studded tire shown but other articles, such as tires without studs and hobnails of a heel of women's shoes, may be used as the grinding member 14. Thus, test results can also be obtained in these cases.

A semicircular sample having a thickness of 40 mm and a weight of 4 kg, produced by adding by 10% additives comprising, for example, 20 to 70 parts of asphalt and 30 to 80 parts of thermoplastic resin to aggregates for use in road to be heated and mixed, by charging the resulting heated additives in a mold frame, by tightening up the mold by means of a rolling pressurization device, and by taking the pressed additives from the mold frame after cooling, can be used as the test piece of road material in this apparatus.

The application of this apparatus is not limited to the above-described road materials but also includes abrasion-resistance testing of all floor materials such as P-tile, vinyl chloride tile, linoleum and wood.

According to the present invention, it is desired to adopt the lower-temperature condition by liquefied nitrogen within a range of $-50°$ to $0°$ C. or the higher-temperature condition by the heating source within a range of $30°$ to $80°$ C. However, the apparatus according to the present invention can be satisfactorily employed to test at a temperature $0°$ to $30°$ C. outside of said lower-temperature range and said higher temperature range.

A preferred embodiment of the present invention will be described below.

At first, the above-described materials were prepared as test road material.

Then, sixteen arcuate pieces of this material were spread over the outer peripheral portion of the turntable of the apparatus.

Subsequently, in order to carry out the abrasion test of these test pieces at a lower temperature of $-15°$ C., the automatic control panel was set at $-15°$ C. and then the turntable was rotated by means of the geared motor and simultaneously a valve connected to the nozzle for use with liquefied nitrogen was opened to so inject nitrogen gas into the chamber followed by carrying out the levelling operation until the test pieces on the turntable reached a temperature of $-15°$ C. as a whole.

After the temperature of the test pieces reached $-15°$ C. in the above-described manner, a load of 300 kg was applied to the studded tire (corresponding to a car of 1.2 tons if having four wheels) and the studded tire was rotated on the test pieces at a speed of 20 km/hr to rotate the main body of the turntable for one hour with the studded tire in contact with the test pieces.

The speed of the apparatus according to the present invention can be regulated within a range of 0 to 50 km/hr but it is desired to test at a speed of 10 to 20 km/hr. Subsequently, the studded tire was raised from the test pieces to investigate the condition of abrasion and shaving of the test pieces by the studded tire.

As described above, with the apparatus according to the present invention, the chamber capable of providing both a cooling temperature and a high temperature is disposed over a semicircumferential portion of the turntable, so that the test piece on the turntable can be set to an appointed temperature simply and in a short time. In addition, the temperature, the rotational speed of the turntable, the rotational speed and load of the studded tire, the test time and the like can all be preset on the automatic control panel, so that tests in various patterns can be simply carried out.

Furthermore, a large number of test pieces can be simultaneously tested so that, if a plurality of test pieces having various kinds of compositions are simultaneously disposed in the turntable, differences in abrasion and the degree of cracking can be found by conducting tests under substantially the same conditions. Thus it can be said that the apparatus according to the present invention is a remarkably suitable tester for use in selecting road material and floor material having the optimum composition.

What is claimed is:

1. An apparatus for testing the degree to which a test piece abrades, said apparatus comprising:
    a turntable rotatably supported in the apparatus, said turntable having a test piece-inserting portion defined thereon for receiving a test piece;
    a cooling or high-temperature chamber confronting said turntable and open to said turntable at a location past which said test piece-inserting portion is moved when said turntable is rotated in the apparatus, said cooling or high-temperature chamber including heating and cooling means selectively operable for allowing the interior of said chamber to be heated and cooled;
    a rotatable grinding member for abrading a test piece received in said test piece-inserting portion; and
    support means supporting said grinding member in the apparatus and for moving said grinding member between a first position at which the grinding member is disposed away from said turntable and a second position at which said grinding member is operative to rotate in contact with a test piece received in said test piece-inserting portion and rotate said turntable, said second position being defined in the apparatus at another location past which said test piece-inserting portion is moved when said turntable is rotated in the apparatus.

2. An apparatus as claimed in claim 1, and further comprising a work table disposed over said turntable and having a diameter smaller than that of said turntable, and wherein the test piece-receiving portion of said turntable is provided outwardly of said work table, said cooling or high-temperature chamber being fixed to said work table.

3. An apparatus as claimed in claim 1, wherein said location at which said cooling or high-temperature chamber confronts said turntable is a semicircular area past which a peripheral portion of said turntable moves when rotated in the apparatus.

4. An apparatus as claimed in claim 1, wherein said support means moves said grinding member up and down relative to said turntable between said second and said first positions.

5. An apparatus for testing the degree to which a test piece abrades, said apparatus comprising:
    a turntable rotatably supported in the apparatus, said turntable having a work table disposed thereover and a test piece-inserting portion defined thereon for receiving a test piece, the work table having a diameter smaller than that of said turntable, and the test piece-receiving portion of the turntable being provided outwardly of said work table;
    a cooling or high-temperature chamber confronting said turntable and open to said turntable at a semicircular area past which a peripheral portion of said turntable moves when the turntable is rotated in the apparatus, said cooling or high-temperature chamber including heating and cooling means selectively operable for allowing the interior of said chamber to be heated and cooled;
    a rotatable grinding member for abrading a test piece received in said test piece-inserting portion; and
    support means supporting said grinding member in the apparatus and for moving said grinding member down and up relative to said turntable between a first position at which said grinding member is disposed away from said turntable and a second position at which said grinding member is operative to rotate in contact with a test piece received in said test piece-inserting portion and rotate said turntable, said second position being defined in the apparatus opposite said location and at another location past which said test piece-inserting portion is moved when said turntable is rotated in the apparatus.

6. An apparatus as claimed in claim 5, wherein said grinding member is a studded tire.

7. An apparatus as claimed in claim 5, wherein said heating and cooling means comprises a nozzle mounted to said chamber for injecting liquefied nitrogen gas into the chamber at a temperature within the range of $-50°$ C. to $0°$ C. and a heater for heating the interior of the chamber to a temperature of within the range of $30°$ C. to $80°$ C.

* * * * *